United States Patent [19]

Duhamel et al.

[11] 4,275,217
[45] Jun. 23, 1981

[54] PROCESS FOR THE PREPARATION OF OPTICALLY ACTIVE α-AMINO ACIDS AND THEIR DERIVATIVES

[75] Inventors: Lucette Duhamel, Mont-Saint-Aignan; Jean-Christophe Plaquevent, Maromme, both of France

[73] Assignee: Agence Nationale de Valorisation de la Recherche (ANVAR), Neuilly sur Seine, France

[21] Appl. No.: 56,106

[22] Filed: Jul. 9, 1979

[30] Foreign Application Priority Data

Jul. 7, 1978 [FR] France .............................. 78 20345

[51] Int. Cl.$^3$ ..................... C07D 233/64; C07B 19/00
[52] U.S. Cl. ........................... 548/344; 260/326.14 T; 260/455 R; 260/465 E; 260/465.4; 260/465.5 R; 560/35; 560/38; 560/40; 560/153; 560/155; 560/168; 560/169; 560/170; 564/164; 564/198; 564/225; 564/246; 564/278

[58] Field of Search ............... 562/401; 260/326.14 T, 260/564 R, 566 F, 465, 465.5 R, 465.4, 558 A, 561 A, 455; 548/344; 560/35, 38, 153, 40, 155, 168, 170, 169; 564/163, 164, 198, 225, 246, 278

[56] References Cited

U.S. PATENT DOCUMENTS

| | | | |
|---|---|---|---|
| 3,803,213 | 4/1974 | Weber et al. ..................... | 562/401 X |
| 3,976,680 | 8/1976 | Clark et al. ...................... | 562/401 X |
| 4,002,666 | 1/1977 | Shirai et al. ...................... | 562/401 X |
| 4,048,224 | 9/1977 | Chemerda et al. ................. | 562/401 |
| 4,111,980 | 9/1978 | Boesten .............................. | 562/401 |

*Primary Examiner*—Robert Gerstl
*Assistant Examiner*—Vera C. Clarke
*Attorney, Agent, or Firm*—Cushman, Darby & Cushman

[57] ABSTRACT

A chiral α-amino acid having a hydrogen substituent in a position alpha to the carboxylic function thereof is prepared by subjecting a corresponding optical antipode with a chiral amino acid to a strong base whereby the proton in a position alpha to the carboxylic function is removed and thereafter reacting the resulting product with a chiral protonation agent.

25 Claims, No Drawings

PROCESS FOR THE PREPARATION OF OPTICALLY ACTIVE α-AMINO ACIDS AND THEIR DERIVATIVES

The present invention relates to a new process for the preparation of optically active α-amino acids, or their derivatives.

BACKGROUND OF THE INVENTION

The preparation of optically active amino acids is important for these materials are used principally in the food and pharmaceutical industries.

The preparation of optically active amino acids by asymmetric synthesis is a known procedure. These processes have principally been the object of a review by K. Weinges and B. Stemmle, Recent Dev. Chem. Nat. Carbon Compd. 1976, 7, 89.

GENERAL DESCRIPTION OF THE INVENTION

The process of the present invention is based on a different principle and comprises a deracemization by enantioselective protonation.

The process of the present invention is simple and quick to carry out. There is no necessity for employing costly or difficult-to-secure catalysts, and the present invention is not limited to substances exhibiting an isomerizing crystallization phenomenon.

DETAILED DESCRIPTION OF THE INVENTION

The present invention thus relates to a process for preparing a chiral α-amino acid or one of its derivatives, having a hydrogen substituent in a position alpha to the carboxylic function or to the derivative thereof, from a corresponding optical antipode or from a mixture of said optical antipodes with said chiral amino acid or its derivative, characterized by the fact that the starting material is subjected to the action of a strong base, in order to remove the proton in a position alpha to the carboxylic function or to the derivative thereof. This proton removal operation is carried out in a manner known per se. Thereafter, the resulting product is reacted with a sterically hindered chiral protonation agent.

The resulting product is solely or predominantly an amino acid or a derivative thereof, having an optical activity different from that of the starting material. One novel feature of the present invention resides then essentially in the theoretical possibility of obtaining a pure enantiomer starting from a racemic mixture or even from its optical inverse, with a maximum yield being able to reach 100% as compared with 50% in the case of resolution.

The initial reactant, in the present invention, can be, for example, an amino acid (or one of its derivatives), generally in the form of a mixture of enantiomers, that is desired to be transformed, or enriched, into one of the enantiomers. Representative amino acids or derivatives thereof, useful as initial reactants, include, for instance, phenylglycine, alanine, phenylalanine, valine, leucine, isoleucine, tyrosine, serine, threonine, methionine, tryptophane, arginine, lysine, histidine and the like, and derivatives thereof.

Representative derivatives of the initial reactant amino acids or of mixtures of enantiomers of amino acids, include, principally, enolizable derivatives of the carboxylic function, such as esters, thioesters, nitriles, amidines, amides, and the like, as well as derivatives of the amine function, such as Schiff bases, acylation derivatives, and more generally amino acid derivatives in which the amine group is transformed with the aid of a protective group capable of being removed to give again the non-protected amine.

Such protective groups are well known and are described for instance by R. A. Boissonnas, Advances In Organic Chemistry, Methods and Results, Vol. 3, Interscience Publishers, 1963, pages 159 and following, as well as by J. F. W. McOmie, idem, pages 191 and following.

Representative temporary protective groups for the amine function, include, e.g., carbo-tert. butyloxy, formyl, phthaloyl and the like. However, the reactive groups, optionally present, other than the α-amino group, can also be protected. This is the case, for example, of the lateral amine group of lysine or of ornithine; of the guanidino group of arginine; of the hydroxyl groups of serine, of threonine and of tyrosine; and of the thiol group of cysteine.

The initial reactant can be, for example, a Schiff base of an ester of an α-amino acid. These Schiff bases can be obtained in accordance with known procedures, for example by reacting an amino acid with thionyl chloride in the presence of an alcohol to form the corresponding amino ester hydrochloride; then by reacting a carbonyl derivative with the said amino ester hydrochloride under conventional conditions for preparing Schiff bases.

Representative carbonyl derivatives include, principally, those of the formula $R_4$—CO—$R_3$, wherein $R_3$ and $R_4$ can represent a hydrocarbon group optionally substituted, with one of $R_3$ and $R_4$ also being able to represent hydrogen.

The expression "Schiff base" herein means not only the derivatives of aromatic aldehydes, but more generally aromatic or aliphatic derivatives of ketones or aldehydes. The substituents $R_3$ and $R_4$ can represent principally aryl, linear or branched alkyl, or cycloalkyl groups, optionally substituted. This latter expression includes groups having heteroatoms.

Generally, the hydrocarbon groups that $R_3$ and $R_4$ represent possess up to 20 carbon atoms. The $R_3$ and $R_4$ substituents, when they represent an aryl group, are principally a phenyl group optionally substituted by an alkoxy group (such as methoxy or ethoxy), or an alkyl (such as isopropyl or methyl), and the like.

The initial reactant can be either a racemic product, or a mixture of enantiomers in any proportions. By the choice of a chiral acid of appropriate configuration, it is possible either to obtain a mixture enriched in one of the enantiomers of the said initial reactant, or to transform one of the enantiomers into its optical antipode.

The expressions "enantiomers" and "optical antipode" are used herein for convenience, and it refers only to the asymmetric carbon in a position alpha relative to the carboxyl group. But it indeed is understood that the process of the present invention is applicable to amino acids possessing other asymmetric carbon atoms, in addition to the alpha carbon.

The process of the invention is applicable principally to amino acids, and their derivatives, having the characteristic group of formula I:

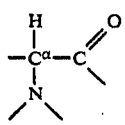

(I)

The products of formula I include principally derivatives of formula IA:

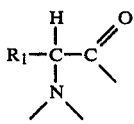

(IA)

wherein $R_1$ is a hydrocarbon group, such as alkyl, aryl or aralkyl, optionally substituted and having, optionally, heteroatoms, and principally, phenyl, benzyl, indole-3-yl methyl, isopropyl, methyl and 2-methylpropyl.

The strong base used in the above defined process is principally one which permits the transformation of the group of formula I, by removal of a proton, into an enolate of formula II:

of formula II:

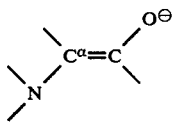

(II)

Representative useful strong bases include, particularly, hydrides, alcoholates and amides; and principally alkaline hydrides, alcoholates or amides, such as the hydrides of sodium, potassium or lithium; lithium or potassium terbutylate; lithium di-isopropylamide and the like. This strong base is generally employed in an amount of at least one equivalent per mole of derivative of formula I.

This enolization reaction is carried out generally in a solvent which preferably is anhydrous. The solvent can be principally an ether such as tetrahydrofuran or ethyl ether, or an alcohol such as t-butanol and the like.

Moreover, it was discovered that the optical yield could be surprisingly increased when the strong base is itself optically active. The optically active strong bases which may be used in the present process are for instance selected from the group consisting of hydrides, alcoholates and amides (e.g. alkali metal hydrides, alcoholates or amides), such that said bases contain one or more asymetric carbon—or hetero—atoms giving rise to an optical activity. An example of an optically active base which may be used is an amide, such as an alkaliamide, e.g. lithium amide, of (+) N-methyl phenylethylamine.

The chiral acids useful in the above process are preferably those which have a sterically hindered group.

Because of the use of such an acid, it is possible to fix a proton in an enantioselective manner on the alpha carbon of the enolate of formula II.

The use of a given sterically hindered chiral acid permits the preferential fixation, on one of the planar faces of the enolic double bond, of a proton, and the use of the optical antipode of this sterically hindered acid, permits the preferential fixation of a proton on the other planar face of the enolic double bond.

The sterically hindered chiral acids are those having at least one cyclic substituent (saturated or unsaturated) or a branched group. The sterically hindered chiral acids can have principally at least one alkyl substituent, preferably branched, optionally substituted or unsaturated (e.g. alkenyl), cycloalkyl or aryl, optionally substituted, or a bridged hydrocarbon substituent, or again carrying a branched alkyl group.

Representative useful acids include principally, diacyltartaric acids and their monoesters, camphanic acid, mandelic acid, 2-phthalimido-3-phenyl propionic acid, 2-trifluoromethyl-2-methoxy phenylacetic acid and the like.

Representative useful chiral acids include, principally, diacyl tartaric acids of formula IV:

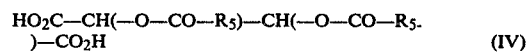

(IV)

wherein $R_5$ is a residue of a carboxylic acid, preferably hindered, and the monoesters of the diacids of formula IV.

The substituent $R_5$ can be, principally, alkyl, preferably branched, optionally substituted or unsaturated (e.g. alkenyl), a cycloalkyl, an aryl, principally phenyl or naphthyl, optionally substituted, or bridged hydrocarbon group, for example, an adamantyl group, and the like.

Representative diacyl tartaric acids of formula IV include principally those which are set forth in the following experimental portion of this disclosure.

All these hindered acids are known or can be prepared in accordance with general methods described in the literature.

For example, to prepare di-adamantyl carboxylate of tartaric acid, 3 moles of the chloride of adamantyl carboxylic acid are mixed with one mole of tartaric acid. The resulting mixture is heated to 140° C. for 2-3 hours; then cooled and subsequently taken up in benzene. The anhydride which crystallizes is separated and then taken up with acetone, to which is then added a stoichiometric amount of water. The resulting mixture is then heated at reflux and the acetone is evaporated, yielding the acid of formula IV, wherein $R_5$=adamantyl.

These chiral acids are employed at a rate of at least one equivalent per mole of derivative of formula I. Generally, an excess of chiral acid is employed, preferably at a rate of two equivalents of chiral acid per mole of derivative of formula I.

The chiral acid is reacted in solution in a solvent; this solvent being, preferably, the same as that used in the enolization reaction.

Preferably, the chiral acid is reacted at a temperature ranging from 0° to −100° C., and more preferably near −70° C., for a time ranging from a few minutes to a few hours. For example, the protonation reaction is generally terminated at the end of 15 minutes at −70° C.

The optically active amino acid derivative is isolated in accordance with known methods. For example, the protonation agent is separated by quantitative formation of a salt insoluble in ether in which the Schiff base remains in solution.

After the protonation reaction, the product obtained can be transformed into any other derivative corresponding to formula I, by known transformation reactions, for example, deprotection, without racemization. For example, a resulting Schiff base of formula III,

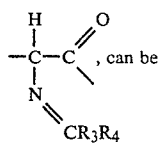  (III)

can be transformed into an amino ester or into a corresponding amino acid in accordance with known methods, by acid hydrolysis. The amino ester can be transformed into an amino acid by alkaline hydrolysis.

Besides, it is possible to recover, with a good yield, and without racemization, the chiral acid such as IV used, in the protonation reaction. A detailed example is given in the experimental portion below.

The following non-limiting examples illustrate the present invention. In all these examples, the procedures are carried out in an inert atmosphere, for example under a nitrogen atmosphere.

EXAMPLE 1

Enantioselective protonation of methyl N-benzylidene phenyl glycinate by L-dipivaloyltartaric acid (Formula IV, $R_5$=t-butyl)

0.5 g ($5 \times 10^{-3}$ M) of diisopropyl amine is dissolved in 15 cm$^3$ of dry tetrahydrofuran. The resulting solution is cooled to $-5°$ C. To this cooled solution at this temperature there are added 3.12 cm$^3$ of 1.6 M n-butyl lithium in solution in hexane ($5 \times 10^{-3}$ M).

The resulting solution is stirred for ¼ hour at a temperature between $-5°$ C. and $0°$ C. and is then cooled to $-70°$ C. At this temperature there is added 0.885 g ($3.5 \times 10^{-3}$ M) of the Schiff base of the methyl ester of racemic phenylglycine, in solution in 6 cm$^3$ of dry tetrahydrofuran. The resulting mixture is agitated for ¼ hour at $-70°$ C. at which time there are added 3.18 g ($1 \times 10^{-2}$ M) of L-dipivaloyltartaric acid in solution in 10 cm$^3$ of dry tetrahydrofuran. After ¼ hour of stirring at $-70°$ C., the reaction mixture is permitted to return to ambient temperature. The solution is treated with 30 cm$^3$ of a saturated NaHCO$_3$ aqueous solution; the organic phase is washed with 30 cm$^3$ of water, dried with magnesium sulfate and concentrated under reduced pressure. The yellow oil obtained (corresponding optically active Schiff base of series L) is crystallized in hexane; the crystals are filtered and dried; yield: 85%. $(\alpha)_D^{25} = -41.8°$. The optical yield is 50%.

Recovery of L-dipivaloyl tartaric acid

The aqueous phase is washed 3 times with 30 cm$^3$ of ether which has been acidified up to pH 1 with a 10% HCl aqueous solution. This aqueous phase is extracted 3 times with 30 cm$^3$ of ether. The resulting organic phase is dried on magnesium sulfate, then filtered, and the solvent is evaporated under the vacuum of a water jet. The colorless oil obtained is crystallized in pentane. The resulting crystals are filtered and dried in a dessicator. (weight obtained = 3.05 g, yield = 96%)

EXAMPLE 2

Enantioselective protonation of the Schiff base of the methyl ester of tryptophane, of Formula III, with $R_3$=H and $R_4$=C$_6$H$_5$.

This protonation operation is carried out essentially in the same manner outlined in Example 1. However, only $1.7 \times 10^{-3}$ M of the racemic Schiff base (0.52 g) is added.

The optically active Schiff base (Series L) with an optical yield of 30.5% is obtained.

EXAMPLE 3

The procedures of Example 1 are again followed and there are employed, as initial reactants, Schiff bases (racemic) of formula III$_x$:

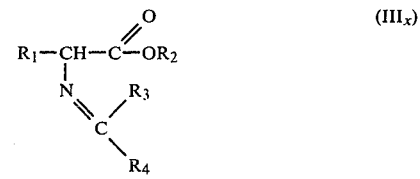  (III$_x$)

wherein $R_1$ is the residue of an $\alpha$-amino acid of the formula: $R_1$—CH(NH$_2$)—CO$_2$H, $R_1$ being a hydrocarbon group, such as alkyl, aryl or aralkyl, optionally substituted and having optionally, heteroatoms, and principally a phenyl, benzyl, indole-3-yl methyl, isopropyl, methyl and 2-methylpropyl group; and $R_2$ is the residue of a $R_2$—OH alcohol, for example an alkyl, aralkyl group or the like.

The formulas of several Schiff bases used in this Example are set forth in Table I, below, ($R_3$=H, $R_4$=phenyl, $R_2$=methyl).

TABLE I

| Schiff Base: III$_x$ with x = | $R_1$ | Characteristics of the pure optical product | |
|---|---|---|---|
| | | Series: | $(\alpha)_D^{25}$ |
| 1 | phenyl | D | +84° (c = 3, CHCl$_3$) |
| 2 | benzyl | L | −245° (c = 4, CHCl$_3$) |
| 3 | indole-3-yl methyl | L | −290° (c = 3, CHCl$_3$) |
| 4 | isopropyl | L | −130° (c = 4, CHCl$_3$) |
| 5 | methyl | L | −100° (liquid) |
| 6 | 2-methyl propyl | | |

The preceding Schiff bases have been enolized, then protonated with the following diacyl tartaric acids (series L) of formula IV (Bu signifies: butyl):

TABLE 2

| Diacid of formula IV$_x$ with x = | $R_5$ |
|---|---|
| 1 | t—Bu |
| 2 | t—Bu—CH$_2$— |
| 3 | t—Bu—(CH$_2$)$_2$— |
| 4 | phenyl |
| 5 | benzyl |
| 6 | phenethyl |
| 7 | (CH$_3$)$_2$—C Br— |
| 8 | cyclohexyl |
| 9 | C$_6$H$_5$—CH=CH— |
| 10 | adamantyl |
| 11 | methyl |
| 12 | isopropyl |
| 13 | n-propyl |
| 14 | (C$_2$H$_5$)$_3$C— |
| 15 | 1,1,3,3-tetramethyl butyl |
| 16 | 2,4,6-trimethylphenyl |
| 17 | $\alpha$-naphthyl |
| 18 | o-tolyl |
| 19 | m-tolyl |
| 20 | 2,5-dimethyl phenyl |

The results obtained with these acids are set forth in Table 3, below:

TABLE 3

| Schiff Base | Acid IV$_x$ with x = | Optical yield, % | Chemical yield, % |
|---|---|---|---|
| III$_1$ | 2 | 16.3 | |
| | 3 | 33.5 | |
| | 4 | 12.3 | |
| | 5 | 8.25 | 80 |
| | 6 | 6.4 | to |
| | 7 | 34.4 | 85 |
| | 8 | 35.8 | |
| | 9 | 25.1 | |
| | 10 | 53.2 | |
| | 11 | 2.6 | |
| | 12 | 12.3 | |
| | 13 | 4.25 | |
| | 14 | 5.45 | |
| | 15 | 11.1 | |
| | 16 | 8.5 | |
| | 17 | 4.5 | |
| III$_2$ | 1 | 27 | |
| | 2 | 8 | |
| | 3 | 17.7 | 60 |
| | 4 | 33.5 | to |
| | 5 | 15 | 65 |
| | 6 | 3 | |
| | 20 | 18.5 | |
| III$_3$ | 2 | 10.7 | |
| | 3 | 14.6 | 90 |
| | 4 | 12.6 | to |
| | 5 | 3.8 | 95 |
| | 6 | 7 | |
| III$_4$ | 1 | 33.5* | 70 |
| | 2 | 21 | to |
| | 4 | 38.5* | 75 |
| | 8 | 35 | |
| | 9 | 20.5 | |
| | 18 | 24.5 | |
| | 19 | 29 | |
| III$_5$ | 4 | 30 | 25% |
| | 19 | 28 | 60% |
| III$_6$ | 1 | 33.3* | 70% | all the products obtained are series L.
* = Result confirmed or determined by NMR with the aid of a chiral salt of europium.

EXAMPLE 4

The racemic Schiff bases, III$_1$–III$_4$ (see the preceding Example) have been enolized, then protonated as before, with various optically active hindered acids. The results are set forth in Table 4, below:

TABLE 4

| Schiff Base | Acid | Optical Yield, % | Serie | Chemical Yield, % |
|---|---|---|---|---|
| III$_1$ | (−) camphanic | 2.7 | D | 80 |
| | (+) mandelic | 2.48 | D | 85 |
| | 2-phthalimido 3-phenyl propionic(L) | 3.9 | L | 80 |
| | (−) 2-methoxy-2 trifluoro methyl phenyl acetic | 14.5 | L | 85 |
| (L) | t—Bu—CO$_2$—CH—CO$_2$H  t—Bu—CO$_2$—CH—CO$_2$CH$_3$ | 19.6 | L | 80 |
| III$_2$ | (+) mandelic | 8.6 | D | 60 |
| III$_3$ | (+) mandelic | 8 | D | 90 |
| III$_4$ | (+) mandelic | 15.1 | D | 75 |

EXAMPLE 5

The racemic Schiff base of the formula: C$_6$H$_5$—CH(—N=CH—t-Bu)—COOCH$_3$, has been enolized, then protonated as before with acids IV$_1$, IV$_3$ and IV$_4$.

By HCl hydrolysis of the resulting optically active Schiff base, there is obtained the hydrochloride of the optically active amino ester of series L, of the formula:

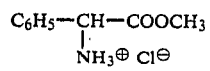

with optical yields of 8.5, 7.5 and 4.7%, respectively. (chemical yields: 60–65%).

EXAMPLE 6

The Schiff base (III, with R$_3$=H and R$_4$=phenyl) of phenylglycine methyl ester was subjected to proton removal with the aid of (+) lithium N-methyl phenylethylamide. Then the corresponding lithium enolate thus obtained was protonated by the action of (L) dipivaloyl tartaric acid. The optically active Schiff base of phenylglycine methyl ester was then recovered (yield 75%) and purified in hexane. Purification yielded 60% of a product which, after acid hydrolysis (yield 95%), gave the corresponding phenylglycine methyl ester hydrochloride:

$[\alpha]_D^{25} = +92.4°$ (CH$_3$OH)

Optical yield: 70.5%.

Ref: (D) phenylglycine methyl ester hydrochloride: $[\alpha]_D^{25} = -131°$ (CH$_3$OH)

What is claimed is:

1. A process for preparing a chiral α-amino acid or a derivative thereof, having a hydrogen substituent in a position alpha to the carboxylic function or a derivative thereof, said process utilizing as an initial reactant a corresponding optical antipode or a mixture thereof with said chiral amino acid or a derivative thereof, said process comprising submitting said initial reactant to the action of a strong base so as to remove the proton in a position alpha to the carboxylic function or derivative thereof, and reacting the resulting product with a sterically hindered chiral protonation agent which is a chiral acid having at least one cyclic substituent or a branched group.

2. The process of claim 1 wherein said amino acid or its derivative is selected from the group consisting of phenylglycine, alanine, phenylalanine, valine, leucine, isoleucine, tyrosine, serine, threonine, methionine, tryptophane, arginine, lysine, histidine and derivatives thereof.

3. The process of claim 2 wherein the derivative of the amino acid or of the mixture of amino acids is an enolizable derivative of the carboxylic function selected from an ester, thioester, nitrile, amidine and amide; a derivative of the amine function in which the amine group is transformed with the aid of a protective group; or an acylation derivative.

4. The process of claim 3 wherein the initial reactant is a Schiff base of alpha amino acid or a derivative thereof.

5. The process of claim 4 wherein said Schiff base results from the reaction of an alpha amino acid or its derivative and a carbonyl compound of the formula R$_4$—CO—R$_3$ wherein R$_3$ and R$_4$ each represent a hydrocarbon group or substituted hydrocarbon group with one of R$_3$ and R$_4$ also being able to represent hydrogen.

6. The process of claim 5 wherein at least one of R$_3$ and R$_4$ represents aryl, linear or branched alkyl, or cycloalkyl.

7. The process of claim 5 wherein said initial reactant is a Schiff base of the formula

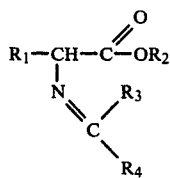

wherein $R_1$ is the residue of an α-amino acid of the formula $R_1$—CH(NH$_2$)—CO$_2$H, $R_2$ is the residue of an alcohol of the formula $R_2$—OH, and $R_3$ and $R_4$ have the meanings given in claim 5.

8. The process of claim 7, wherein $R_1$ represents a hydrocarbon group selected from alkyl, aryl or aralkyl group.

9. The process of claim 8 wherein $R_1$ represents phenyl, benzyl, indole-3-yl methyl, isopropyl, methyl or 2-methylpropyl.

10. The process of claim 1 wherein said strong base is selected from the group consisting of a hydride, an alcoholate and an amide.

11. The process of claim 10 wherein said strong base is employed in an amount of at least one equivalent per mole of starting amino acid, or its derivative.

12. The process of claim 1 wherein the reaction with the strong base is carried out in an anhydrous solvent.

13. The process of claim 12 wherein said solvent is an ether or an alcohol.

14. The process of claim 1 wherein said sterically hindered chiral acid has at least one alkyl, cycloalkyl or aryl substituent, or a bridged hydrocarbon substituent carrying at least one branched alkyl group.

15. The process of claim 1 wherein said chiral acid is selected from the group consisting of diacyltartaric acid and its monoester, camphanic acid, mandelic acid, 2-phthalimido-3-phenyl propionic acid and 2-trifluoromethyl-2-methoxy phenylacetic acid.

16. The process of claim 15 wherein said chiral acid is diacyltartaric acid of the formula:

HO$_2$C—CH(—O—CO—R$_5$)—CH(—O—CO—R$_5$)—CO$_2$H wherein $R_5$ is the residue of a carboxylic acid or the monoester of said diacid.

17. The process of claim 16 wherein $R_5$ is alkyl, alkenyl, aryl, or a bridged hydrocarbon group.

18. The process of claim 17 wherein $R_5$ represents methyl, n-propyl, isopropyl, t-butyl, neopentyl, 3,3-dimethylbutyl, phenyl, benzyl, phenethyl, (CH$_3$)$_2$—CBr—, cyclohexyl, styryl, adamantyl, (C$_2$H$_5$)$_3$C—, 1,1,3,3-tetramethyl butyl, 2,4,6-trimethyl phenyl, α-naphthyl, o-tolyl, m-tolyl or 2,5-dimethyl phenyl.

19. The process of claim 1 wherein the said chiral acid is reacted at a rate of at least one equivalent per mole of derivative of amino acid.

20. The process of claim 19 wherein the said chiral acid is reacted in solution in a solvent.

21. The process of claim 19 wherein the chiral acid is reacted at a temperature ranging from 0° to −100° C.

22. The process of claim 21 wherein the chiral acid is reacted at a temperature of about −70° C.

23. The process of claim 1 wherein said strong base is optically active.

24. The process of claim 23 wherein said optically active base is an amide of (+) N-methyl phenylethylamine.

25. A process for preparing a chiral α-amino acid or a derivative thereof, having a hydrogen substituent in a position alpha to the carboxylic function or a derivative thereof, said process utilizing as an initial reactant a corresponding optical antipode or a mixture thereof with said chiral amino acid or derivative thereof, said process comprising submitting said initial reactant to the action of a strong base selected from the group consisting of a hydride, an alcoholate and an amide in, as an anhydrous solvent, an ether or an alcohol at a temperature ranging from 0° to −100° C. so as to remove the proton in a position alpha to the carboxylic function or derivative thereof, and reacting the resulting product with a sterically hindered chiral protonation agent which is a chiral acid selected from the group consisting of diacyl tartaric acid and its monoester, camphanic acid, mandelic acid, 2-phthalimido-3-phenyl propionic acid and 2-trifluoromethyl-2-methoxy phenylacetic acid.

* * * * *